United States Patent [19]
Goddard et al.

[11] Patent Number: 5,352,823
[45] Date of Patent: Oct. 4, 1994

[54] PROCESS FOR IMPROVING FLOW CHARACTERISTICS OF CRYSTALLINE IBUPROFEN

[75] Inventors: Lloyd E. Goddard, Orangeburg; George A. Knesel, Columbia, both of S.C.

[73] Assignee: Albemarle Corporation, Richmond, Va.

[21] Appl. No.: 963,872

[22] Filed: Oct. 20, 1992

Related U.S. Application Data

[63] Continuation of Ser. No. 734,910, Jul. 24, 1991, abandoned, which is a continuation-in-part of Ser. No. 615,348, Nov. 19, 1990, abandoned.

[51] Int. Cl.$^5$ .................. C07C 51/43; C07C 51/42
[52] U.S. Cl. ................................. 562/494; 562/493
[58] Field of Search ........................ 562/493, 494

[56] References Cited

U.S. PATENT DOCUMENTS

| | | | |
|---|---|---|---|
| 4,107,439 | 8/1978 | Walker et al. | 560/55 |
| 4,135,051 | 1/1979 | Walker | 560/105 |
| 4,476,248 | 10/1984 | Gordon et al. | 562/494 |
| 4,582,577 | 4/1986 | Wagenknecht | 204/59 R |
| 4,948,805 | 8/1990 | Ziggiotti et al. | 514/428 |

*Primary Examiner*—Jose' G. Dees
*Assistant Examiner*—B. Frazier
*Attorney, Agent, or Firm*—Richard J. Hammond

[57] ABSTRACT

A process for producing crystalline ibuprofen having a crystal habit characterized by a particle length larger than 75 microns average and a length to width aspect ratio of greater than about 4 to 1 to about 5 to 1. The process involves crystallizing ibuprofen from a saturated solution of ibuprofen in a liquid hydrocarbon solvent by seeding and cooling such solution to a temperature of about 0° C. to about −20° C. at a rate to retard primary nucleation and promote secondary nucleation. The crystalline ibuprofen is separated from the slurry produced from such cooling.

12 Claims, 2 Drawing Sheets

PROCESS FOR IMPROVING FLOW CHARACTERISTICS OF CRYSTALLINE IBUPROFEN

This is a continuation of application Ser. No. 07/734,910, filed Jul. 24, 1991 now abandoned, which is a continuation-in-part of application Ser. No. 615,348, filed Nov. 19, 1990, of Lloyd E. Goddard, et al., for "Process for Improving Flow Characteristics of Crystalline Ibuprofen" now abandoned.

FIELD OF THE INVENTION

This invention relates to crystalline ibuprofen having improved physical properties over previously known crystalline ibuprofen materials. More particularly, this invention provides an improved process for preparing crystalline ibuprofen of larger average particle length and improved flow properties.

BACKGROUND OF THE INVENTION

It is well known that alpha-arylalkanoic acids represent a large class of compounds, many of which are useful as anti-inflammatory and analgesic drugs.

Among these, 2-(4-isobutylphenyl)-propionic acid known as Ibuprofen, 2-(3-phenoxyphenyl)-propionic acid known as Fenoprofen, 2-(2-fluoro-4-diphenyl)-propionic acid known as Flurbiprofen, 2-[4-(2-thienylcarbonyl)-phenyl]-propionic acid known as Suprofen, 2-(6-methoxy-2-naphthyl)-propionic acid, whose S(+) isomer is known as Naproxen, and still others may be mentioned.

The preparation of $\alpha$-aryl propionic acids has so far followed the so-called classic chemical methods which employ as starting material aryl alkyl ketone derivatives and are known by such names as Darzen's reaction, Willgerodt's reaction, Arndt-Eistert's reaction and Friedel-Crafts reaction. Of these, Darzen's reaction constitutes more or less the generally accepted basic method for the preparation of $\alpha$-aryl propionic acids. [D. R. White (The Upjohn Company) U.S. Pat. No. 3,975,431 (1976); Chemical Abstracts 86,5168 w].

More recently, newer methods have been proposed for the preparation of $\alpha$-aryl propionic acids. These include Gassman's procedure and certain nucleophilic substitution and chemical rearrangement of propionic acid derivatives [P. G. Gassman and T. J. Van Bergen, *Journal of the American Chemicals Society*, 96(17), 5508 (1974); G. P. Stahly, B. C. Stahly and K. C. Lilge, *Journal of Organic Chemistry*, 49 579 (1984); M. S. Newman and B. J. Magertein, *Organic Reactants V*, 413 (1949); Brown, E. V. Synthesis, 358 (1975); S. Yoshimura, S. Takahashi and M. Ichino (Kohjin Company), Japanese Pat. No. 76,36,432 (Mar. 27, 1976); and Chemical Abstract 85,123596 m].

While any of these preparation schemes produce the desired aryl propionic acid, very little attention has been paid to the methods of processing the materials produced. Thus, one of the highest commercial volume profen drugs, ibuprofen, is typically produced in a crystalline form that flows poorly. (It should be noted that ibuprofen crystalline flow is directly related to total surface area and, therefore, crystal size, i.e. large crystals, promotes flow because of decreased surface area.) As a result, preparations containing this material disadvantageously adhere to the molding surfaces of tablet punches and dies during processing.

In U.S. Pat. No. 4,476,248, incorporated herein by reference, the course of the above disadvantageous behavior was established as due to the size and the shape of the ibuprofen crystals. This patent discloses that acicular (needle) or lath (blade) crystals are to be avoided and cubic or spherical shapes are desirable. These latter shapes produce greatly enhanced crystalline flow properties of the final ibuprofen. The patent further discloses that when ibuprofen is dissolved in and crystallized from a solution of any solvent which has a hydrogen bonding parameter (SH) equal or greater than ($\geq$) 8 Hilderbrand units, e.g., a $C_1$ to $C_3$ alkanol, there is obtained crystalline ibuprofen having larger particle size, on average, as compared to crystalline ibuprofen obtained by crystallizing ibuprofen from heptane or hexane, the usual commercially used solvents.

While this patent extols the economic advantages of such improved flow produced from the larger particle size crystalline ibuprofen, the extra processing step, i.e., the step required to-first remove the inert solvent (typically a hydrocarbon one) used in the above-disclosed processes for preparing the $\alpha$-aryl propionic acid, is undesirably costly and time and equipment consuming.

Accordingly, there is a need for preparing crystalline ibuprofen that has improved flow properties over that of the prior art.

OBJECTS OF THE INVENTION

It is an object of this invention to produce an improved crystalline habit and crystal shape of ibuprofen, and to provide a process for preparing crystalline ibuprofen which has larger average particle length and improved flow properties compared to previously known bulk ibuprofen materials.

It is a further object of this invention to provide a crystalline ibuprofen which has larger average particle size range, having excellent flow properties, and the majority of said particles being rod-shaped crystals.

Other objects, aspects and advantages of this invention will become apparent from reading the remaining specification and the claims which follow.

SUMMARY OF THE INVENTION

Briefly, it has been found that when ibuprofen is dissolved in and crystallized from a saturated solution of a liquid hydrocarbon solvent in a specific procedure, there is obtained crystalline ibuprofen having larger particle length, on average, as compared to crystalline ibuprofen obtained by crystallizing ibuprofen from heptane or hexane as carried out by the conventional forms of commercial processing.

The crystalline ibuprofen obtained by the process of the present invention is recovered without the necessity of first removing the inert solvent disclosed in the prior art to provide crystalline ibuprofen. Such crystalline ibuprofen is subject to further recrystallization and purification utilizing a different solvent.

As a result of the process of the invention, a more cost effective manufacturing process can be developed by, reducing pharmaceutical production down time, due to compressing problems (sticking and lamination), requiring less formulation time and handling, and eliminating energy cost required in the drying operations.

Thus, using the process of this invention in the crystallization of ibuprofen has improved its physical properties and the manufacturability of ibuprofen.

PHOTOMICROGRAPHS

DETAILED DESCRIPTION OF THE PREFERRED EMBODIMENTS

Figure 1:
FIGS. 1, 2, 3 and 4 are microscopic photographic exhibits of ibuprofen crystals prepared by the process of the present invention.

According to the process of the present invention, crystalline ibuprofen has been prepared having a crystalline habit characterized by having a particle length larger than about 75 microns average and a length to width aspect ratio of greater than about 4 to 1 to about 5 to 1. Preferably the particle length is from about 100–200 microns, most preferably from about 125 to about 175 microns. Preferred length to width ratios are from about 4.1 to 1 to about 5 to 1.

In the ibuprofen manufacturing processes, ibuprofen is crystallized from its reaction mixtures by precipitating it from an aqueous solution of the sodium ibuprofen salt, for example, by addition to that salt solution of an inorganic acid or from aqueous/heptane or aqueous/methylene chloride mixture, as known in the art. The ibuprofen crystals produced in this way have a crystal aspect ratio averaging greater than 6. In contrast, according to this invention, we have discovered how to obtain ibuprofen crystals having a crystal aspect ratio averaging no greater than about 5 and as low as 4, for example, (after ibuprofen has been manufactured as above) by dissolving ibuprofen in the defined solvent media used in the process of this invention without any substantial salt formation, and crystallizing the ibuprofen therefrom as described herein to obtain significantly improved crystal habit ibuprofen.

Examples of liquid solvents for ibuprofen which will give the desired low aspect ratio ibuprofen crystal habit include the hydrocarbon solvents which include the linear and branched hydrocarbons having the general formula $C_nH_{2n+2}$, where n is from 5 to 10, preferably from 6 to 8, most preferably 6 or 7. Particularly preferred is hexane. Mixtures of these hydrocarbon solvents may also be used in the process of this invention.

The crystalline ibuprofen having the above-mentioned improved physical properties can be prepared by crystallizing or precipitating the ibuprofen from one or more of the above solvents by a number of methods. A preferred method can be described by the following sequence of steps:

(a) forming a saturated solution of ibuprofen in one or more of the liquid hydrocarbon solvents disclosed herein at a temperature of from about 20° C. to about 60° C.;

(b) seeding the saturated solution with solid ibuprofen;

(c) cooling the saturated and seeded solution to a temperature of about 0° to about −20° C. at a rate to retard primary nucleation and promote secondary nucleation, thereby obtaining a slurry; and (d) separating crystalline ibuprofen from the liquid phase of the slurry.

In carrying out the process of the present invention, it is important to first form a fully ibuprofen-saturated solution in the liquid hydrocarbon solvent. At 20° C., the amount of ibuprofen that forms a fully saturated solution using, for example, the liquid hydrocarbon hexane, is 7.3 grams/100 grams of solvent. At 60° C., 245 grams of ibuprofen fully saturate 100 grams of hexane.

To the fully saturated solution of ibuprofen is then added seed crystals of ibuprofen. The crystal habit of the seed crystals is not important in controlling the formation of the final large, rod-like crystals of the present process. Thus, seed crystals obtained from crystallization of ibuprofen from cooled supersaturated solutions (typically of the acicular or lath shape) and smaller than 20 microns may be used. Equally successful are crystals obtained by crushing the product produced from the cooled supersaturated solutions. Significantly, it has been discovered that primary nucleation of the seeded solution saturated with ibuprofen can be avoided during the cool down sequence if no more than 1.0% by weight of solid ibuprofen based on weight of saturated solution is added, but at least 0.01% by weight of solid ibuprofen based on total weight of saturated solution. Preferably, about 0.015 % by weight to about 0.5% by weight of seed crystals is added, most preferably about 0.02% by weight to about 0.04% by weight. Primary nucleation is defined as spontaneous and/or self-seeding types of nucleation. Secondary nucleation occurs when crystal growth is induced by addition of crystal nuclei, e.g., ibuprofen crystallites.

While the fully saturated and seeded solution of ibuprofen can be cooled down to about 0° C. to about −20° C. in one continuous step over a period of up to 6 hours, it has been found advantageous to conduct such cooling to such lower temperatures in specific time/temperature intervals. Thus, a first cooling interval requires the temperatures to be lowered by about 5 percent and held for about 10 minutes to about 180 minutes, preferably about 20 minutes to about 120 minutes, most preferably about 45 minutes to about 75 minutes. By this sequential lowering, a second and third temperature reduction by a similar amount and for about the same time is necessary before the last, and greatest, temperature reduction to about 0° C. to about −20° C. Such cooling is preferentially carried out under conditions of agitation (stirring, rocking, etc.).

Separation of the slurry produced from the sequential cooling can be accomplished by any conventional method, i.e., filtration, centrifugation, etc.

The invention is further exemplified by the following detailed examples, which are not intended as limiting the scope of the process of this invention.

EXAMPLES

Comparative

Figure 5:
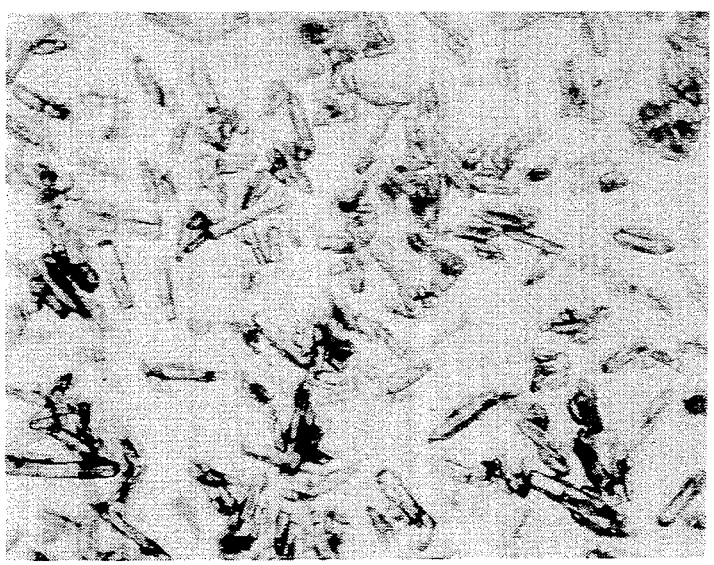
FIG. 5 is a microscopic photographic exhibit of ibuprofen crystals prepared by the process of the prior art.

A commercial batch of ibuprofen was prepared from 43% solution of ibuprofen in hexane. The solution was cooled to 40° C. and seeded with ibuprofen. The mixture was cooled at 5° C./hour to 30° C. and then cooled at 10° C./hour to −10° C. The slurry was centrifuged and the crystals were washed with cold hexane and vacuum dried in a ribbon dryer. The ibuprofen had poor flow characteristics with a strong lumping tendency. The photomicrograph of the crystals showed an average crystal length of 59 microns and an average width of 16 microns, with an average aspect (l/w) of 3.7. (FIG. 5)

EXAMPLE 1

To 309 g of a 43% solution of crude ibuprofen in hexane 0.02 g of seed (smaller crystals of ibuprofen from hexane crystallization) was added at 42° C. The temperature was dropped to 40° C. and held for one hour; the temperature was dropped to 38° C. and held for one hour; and the temperature was dropped to 36° C. and held for one hour. The resultant mixture was then cooled to −10° C. in 180 minutes. The crystals were filtered, washed with cold hexane and dried. The crystals were free flowing with little lumping tendency observed.

Figure 2:

Photomicrographs of the crystals were taken 100 X and the crystal dimensions were measured. The average crystal length was 161 microns, the average width was 38, with an aspect ratio (L/W) of 4.2. (FIG. 2)

EXAMPLE 2

To 283 g of a 43% solution of ibuprofen in hexane 0.02 g of seed (smaller crystals of ibuprofen from hexane crystallization) was added at 42° C. The temperature was dropped to 40° C. and held for 30 minutes and then the temperature was dropped to 36° C. and held for one hour. The resultant mixture was then cooled to −10° C. in three hours. The crystals were filtered, washed with cold hexane and dried. The crystals were free flowing with little lumping tendency observed.

Figure 3:

Photomicrographs of the crystals were taken at 100 X and the crystal dimensions were measured. The average crystal length was 181 microns, the average width was 39, with an aspect ratio (L/W) of 4.6. (FIG. 3)

EXAMPLE 3

Figure 4:
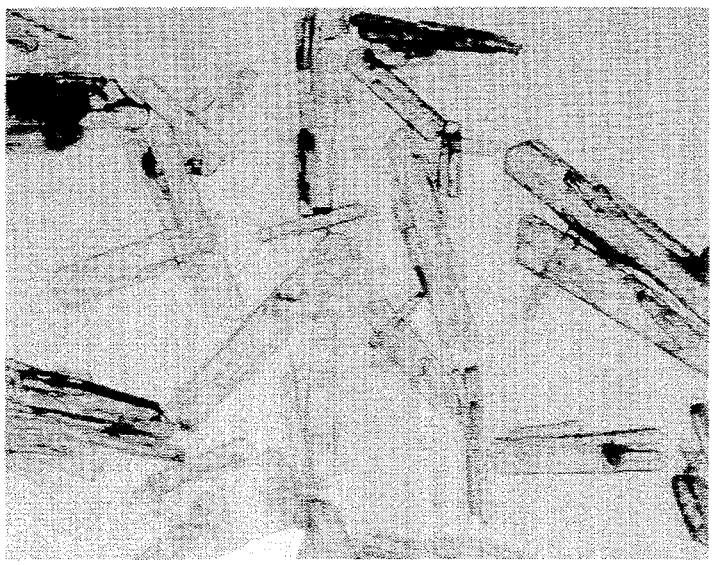

A solution of 128 g of ibuprofen in 170 g of commercial hexane was cooled from 50° C. to 42° C. and seeded with 0.02 g of ibuprofen. The temperature was lowered to 40° C. and held for 30 minutes. The temperature was then lowered to 38° C. and held for 30 minutes, and then lowered to 36° C. and held for 30 minutes. The slurry was cooled to −6° C. over 3-hour period. The slurry was suction filtered and the crystals were washed with cold hexane and air dried. The ibuprofen was free flowing with little lumping tendency. The photomicrograph of the crystals show an average crystal length of 148 microns and an average width of 29 microns, with an average aspect (1/w) of 5.1. (FIG. 4)

We claim:

1. In a process for preparing crystalline ibuprofen by forming a saturated solution of ibuprofen in a hydrocarbon solvent seeding such saturated solution with solid ibuprofen; and cooling the seeded saturated solution below the saturation point to effect crystallization and precipitating the crystalline ibuprofen from the solution thereof, the improvement comprising (a) carrying out said cooling by reducing the temperature of said saturated solution in three sequential steps by about 5% in each step and holding said reduced temperature for about 10 minutes to about 180 minutes for each of said three sequential steps then reducing the temperature of the solution resulting from the third sequential step to about 0° to about −20°, and (b) precipitating crystalline ibuprofen having a crystal habit characterized by having a particle length larger than 150 microns average and a length to width aspect ratio of from about 4.1 to 1 to about 5 to 1.

2. The process according to claim 1 wherein said liquid hydrocarbon is selected from the group consisting essentially of pentane, hexane, heptane, octane and mixtures thereof.

3. The process according to claim 2 wherein said liquid hydrocarbon is hexane, heptane or mixtures thereof.

4. The process according to claim 3 wherein said liquid hydrocarbon is hexane.

5. The process according to claim 1 wherein said temperature of said saturated solution is about 30° C. to about 50° C.

6. The process according to claim 5 wherein said temperature is about 40° C. to about 45° C.

7. The process according to claim 1 wherein the amount of said seeding is about 0.01% to about 1.0% by weight of solid ibuprofen based on the total weight of solution.

8. The process according to claim 7 wherein the amount of said seeding is about 0.015% to about 0.5% by weight.

9. The process according to claim 8 wherein the amount of said seeding is about 0.02% to about 0.04% by weight.

10. The process according to claim 1 wherein said saturated solution with solid ibuprofen is agitated.

11. The process according to claim 1 wherein each one of said three sequentially lower temperatures is carried out over an interval of from about 20 minutes to about 120 minutes.

12. The process according to claim 12 where each of said three sequentially lower temperatures is carried out over an interval of from about 45 minutes to about 75 minutes.

* * * * *

UNITED STATES PATENT AND TRADEMARK OFFICE
CERTIFICATE OF CORRECTION

PATENT NO. : 5,352,823

DATED : October 4, 1994

INVENTOR(S) : Lloyd E. Goddard and George A. Knesel

It is certified that error appears in the above-indentified patent and that said Letters Patent is hereby corrected as shown below:

Column 6, Line 46, reads "... to claim 12 where ..." and should read

-- to claim 11 where --.

Signed and Sealed this

Seventh Day of February, 1995

Attest:

BRUCE LEHMAN

Attesting Officer        Commissioner of Patents and Trademarks